United States Patent
Panella et al.

(10) Patent No.: US 9,377,451 B2
(45) Date of Patent: Jun. 28, 2016

(54) SENSOR ASSEMBLY AND METHOD FOR SENSING STATUS CONDITION OF ELECTRICAL EQUIPMENT

(71) Applicant: ABB RESEARCH LTD, Zürich (CH)

(72) Inventors: Barbara Panella, Wettingen (CH); Jacobus Lodevicus Martinus Van Mechelen, Regensdorf (CH); Robin Gremaud, Olten (CH); Pierre Lorin, Granois (CH)

(73) Assignee: ABB Research Ltd., Zurich (CH)

( * ) Notice: Subject to any disclaimer, the term of this patent is extended or adjusted under 35 U.S.C. 154(b) by 0 days.

(21) Appl. No.: 14/218,321

(22) Filed: Mar. 18, 2014

(65) Prior Publication Data

US 2014/0273261 A1  Sep. 18, 2014

(30) Foreign Application Priority Data

Mar. 15, 2013 (EP) .................................. 13159439

(51) Int. Cl.
| | |
|---|---|
| *G01N 21/84* | (2006.01) |
| *G01N 21/00* | (2006.01) |
| *G01N 33/28* | (2006.01) |
| *H01F 27/40* | (2006.01) |

(52) U.S. Cl.
CPC ......... *G01N 33/2841* (2013.01); *G01N 21/8483* (2013.01); *G01N 21/84* (2013.01); *H01F 27/402* (2013.01); *Y10T 436/22* (2015.01)

(58) Field of Classification Search
CPC ... G01N 33/2841; G01N 33/28; G01N 33/26; G01N 33/2835; G01N 33/00; G01N 21/77; G01N 21/7703; Y10T 436/22; Y10T 436/00
USPC .............. 436/144; 422/82.05, 82.02, 68.1, 50
See application file for complete search history.

(56) References Cited

U.S. PATENT DOCUMENTS

| | | | |
|---|---|---|---|
| 6,289,716 B1 | 9/2001 | Lindgren | |
| 6,834,536 B2 * | 12/2004 | Kempe | ........................ 73/61.41 |
| 2004/0112764 A1 | 6/2004 | Stokes et al. | |
| 2007/0144236 A1 | 6/2007 | Stokes et al. | |
| 2008/0024761 A1 | 1/2008 | Kong et al. | |
| 2012/0214249 A1 | 8/2012 | Belongia | |

OTHER PUBLICATIONS

Search Report mailed on Jun. 28, 2013, by the European Patent Office for Application No. 13159439.2.
Ma et al., "High sensitive and reliable fiber Bragg grating hydrogen sensor for fault detection of power transformer", Sensors and Actuators B: Chemical: International Journal Devoted to Research and Development of Physical and Chemical Transducers, Apr. 2012, vol. 169, pp. 195-198.
Slaman et al., "Optical hydrogen sensors based on metal-hydrides", Proc. of SPIE vol. 8368, 2012 (month unknown), pp. 1-8.
Butler et al., "Fiber Optic Hydrogen Sensor", Sandia Report, SAND96-1133, UC-706, May 1996, pp. 1-51.

* cited by examiner

*Primary Examiner* — Christine T Mui
(74) *Attorney, Agent, or Firm* — Taft Stettinius & Hollister LLP

(57) ABSTRACT

A sensor assembly is disclosed for sensing a status condition of a liquid-filled electrical equipment such as a transformer. The sensor assembly can include a light source; a first hydrogen detection section, the first hydrogen detection section being optically coupled to the light source for receiving light from the light source, wherein the first hydrogen detection section has a first hydrogen sensitive layer that changes an optical response with respect to the received light depending on whether an amount of hydrogen at the first hydrogen sensitive layer is above or below a first threshold; and a first output section optically coupled to the first hydrogen detection section for receiving light having interacted with the first hydrogen sensitive layer such that the received light depends on the optical response of the first hydrogen sensitive layer.

17 Claims, 3 Drawing Sheets

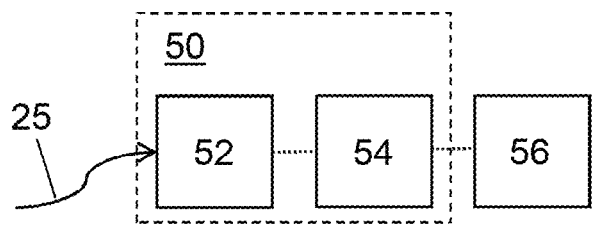
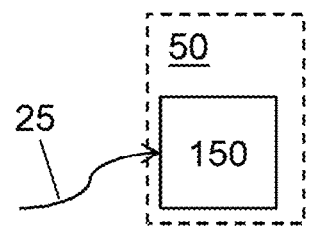
FIG. 4a            FIG. 4b
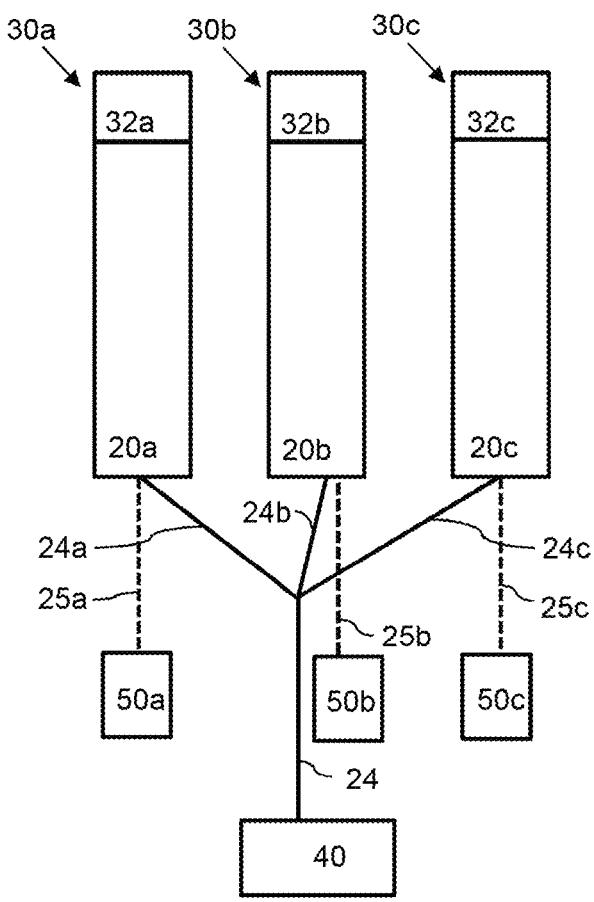
FIG. 7

SENSOR ASSEMBLY AND METHOD FOR SENSING STATUS CONDITION OF ELECTRICAL EQUIPMENT

RELATED APPLICATION

This application claims priority under 35 U.S.C. §119 to European Patent Application No. 13159439.2.8 filed in Europe on Mar. 15, 2013, the entire content of which is hereby incorporated by reference in its entirety.

FIELD

The present disclosure relates to a sensor assembly for liquid-filled electrical equipment such as an oil-filled transformer. The sensor assembly is configured for sensing a status condition of the electrical equipment, e.g. a fault condition. The status condition is obtained by optical determination of a hydrogen content of an insulation liquid of the electrical equipment. Other aspects of the present disclosure relate to methods of use of the sensor assembly, and to methods of sensing a status condition of a liquid-filled electrical equipment.

BACKGROUND INFORMATION

Insulation-liquid-filled electrical equipment, such as oil-filled disconnectors, circuit breakers, and especially transformers such as power and distribution transformers (and/or instrument transformers), are filled with insulation liquid, such as oil, for cooling and electrical insulation purposes. Faults inside the electrical equipment as well as degradation of the insulation liquid and of other insulation components such as insulation paper provided within the electrical equipment can form larger amount of gasses than under normal conditions, which dissolve into the liquid. Hence, measuring the dissolved gas concentration gives information about the "health condition" of these electrical equipment.

Transformers and the other electrical equipment mentioned above are important components of the electrical grid, and their failure can be very costly. A transformer is supposed to operate continuously and as error-free as possible over many years or even decades. Hence, it is important to detect faults, malfunctions and degradation, so that errors that may eventually cause failure of the electrical equipment can be detected in time to take appropriate counter-measures.

As already mentioned, faults in insulation liquid-filled transformers and other electric equipment can be accompanied by the development of larger amounts of gases dissolved in the insulation liquid. The quantity and composition of the decomposition gases is dependent on the underlying defect: A large fault with high energy content, such as rapid overheating or arcing, causes large amounts of gas to be produced in a short period of time, whereas the amount of gas produced by a small fault may be relatively smaller.

According to the IEEE Guide for the Interpretation of Gases Generated in Oil (IEEE C57.104), the status conditions (risk or fault condition) can be classified in transformers according to four conditions that depend on the concentration of dissolved gases. Table 1 shows hydrogen concentration according to the respective classified conditions.

TABLE 1

| Status condition | Hydrogen ($H_2$) content in insulation liquid (ppm) |
| --- | --- |
| status condition 1 | ≤100 |
| status condition 2 | 101-700 |
| status condition 3 | 701-1800 |
| status condition 4 | >1800 |

Thus, if the nature and amount of individual gases dissolved in the insulation liquid are known, this information can be used to identify the type and severity of the corresponding electrical fault in the equipment, e.g. according to these standardized health conditions 1 to 4.

To verify the health status of the insulation liquid of such electrical equipment, two main methods are known: According to a first known method, also referred to as the offline-method, samples of the insulation liquid are regularly (e.g. yearly) taken on-site and analyzed in a specialized laboratory by dissolved gas analysis. However, this offline-method can be burdensome and does not allow obtaining real-time data, and is of no further interest here even though it is a widely used method.

According to a second known method, also referred to as online-method, measurements monitor the gas concentration in the insulation liquid directly and (quasi-)continuously. These on-line sensors include semiconductor sensors, thermal-conductivity analyzers, pellistors and fuel cell sensors, among others. These sensing techniques can involve a complicated gas separation system that adds complexity and cost to the sensor design and calibration.

However, even though the known online systems allow detailed hydrogen concentration values to be obtained, some drawbacks and obstacles remain, such as complex sensor design, problems due to sensor aging and drift, an issue of calibrating and periodically re-calibrating the sensor, high cost, high maintenance requirements and/or limited life-time reliability of the sensors.

Optical hydrogen sensors to be used in transformer oil were previously investigated by M. Slaman, R. Westerwal, H. Schreuders, B. Dam [Proc. SPIE Vol. 8368 836805-1, 2012] and by M. A. Butler, R. Sanchez, G. R Dulleck [Sandia Report Sand 96-113]. In both reports it is proposed to develop a continuous hydrogen sensor that has an almost linear or continuous optical output over a whole hydrogen concentration range.

Another optical hydrogen sensor to be tested in transformer oil was investigated by GUO-MING M A ET AL: "High sensitive and reliable fiber Bragg grating hydrogen sensor for fault detection of power transformer", SENSORS AND ACTUATORS B: CHEMICAL: INTERNATIONAL JOURNAL DEVOTED TO RESEARCH AND DEVELOPMENT OF PHYSICAL AND CHEMICAL TRANSDUCERS, ELSEVIER S.A, SWITZERLAND, vol. 169, 20 Apr. 2012 (2012 Apr. 20), pages 195-198, XP028520709, ISSN: 0925-4005. The optical sensor uses a fiber Bragg grating (FBG) sheathed with an intermediate polyimide and Ti layer and an outermost Pd layer to absorb hydrogen. The absorbed hydrogen induces a strain change on the FBG which results in a continuous wavelength shift response to hydrogen concentration.

SUMMARY

A sensor assembly is disclosed for sensing a status condition of a liquid-filled electrical equipment, the sensor assembly comprising: a light source; a first hydrogen detection section the first hydrogen detection section being optically coupled to the light source for receiving light from the light source, wherein the first hydrogen detection section has a first hydrogen sensitive layer that changes an optical response with respect to received light depending on whether an amount of hydrogen at the first hydrogen sensitive layer is above or below a first threshold; and a first output section optically coupled to the first hydrogen detection section for receiving light having interacted with the first hydrogen sensitive layer such that received light depends on the optical response of the first hydrogen sensitive layer, the first output section being configured for outputting an output signal as a low-hydrogen output signal when the optical response corresponds to an amount of hydrogen below the first threshold, and as a high-hydrogen output signal, different from the low-hydrogen output signal, when the optical response corresponds to an amount of hydrogen above the first threshold, wherein the optical response is at least one of a reflection and a transmission of the first hydrogen sensitive layer.

A method is disclosed of sensing a status condition of a liquid-filled electrical equipment, the method comprising: a first hydrogen detection section in communication with an insulation liquid of the electrical equipment with light, whereby a first hydrogen sensitive layer of the first hydrogen detection section interacts with the light, such that an optical response of the first hydrogen sensitive layer to received light depends on whether an amount of hydrogen dissolved in the insulation liquid is above or below a first threshold; supplying a first output section with the light that has interacted with the first hydrogen sensitive layer, whereby light received by the output section depends on the optical response of the first hydrogen sensitive layer; and if the optical response corresponds to an amount of hydrogen below the first threshold, outputting via the first output section a low-hydrogen output signal, and if the optical response corresponds to an amount of hydrogen above the first threshold, outputting via the first output section a high-hydrogen output signal, different from the low-hydrogen output signal, the optical response being at least one of a reflection and a transmission of the first hydrogen sensitive layer.

BRIEF DESCRIPTION OF THE DRAWINGS

More details will be described in the following with reference to the figures, wherein:

FIGS. 4a and 4b are schematic views of output sections of sensor assemblies according to respective exemplary embodiments disclosed herein;

FIG. 7 is a schematic view of a sensor assembly according to an exemplary embodiment disclosed herein having multiple hydrogen detection sections.

DETAILED DESCRIPTION

Figure 1:
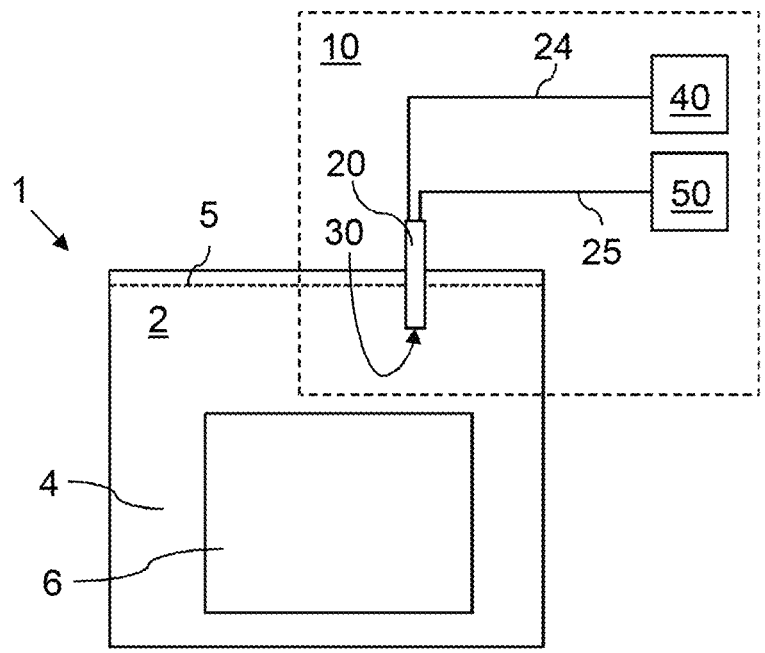
FIG. 1 is a schematic view of an exemplary transformer filled with an insulation liquid in which a sensor assembly according to an exemplary embodiment disclosed herein is immersed.

A sensor assembly is described herein for sensing a status condition of a liquid-filled electrical equipment, such as a transformer. An exemplary sensor assembly can include a light source; a first hydrogen detection section, the first hydrogen detection section being optically coupled to the light source for receiving light from the light source; and a first output section. The first hydrogen detection section has a first hydrogen sensitive layer that changes an optical response with respect to the received light depending on whether an amount of hydrogen at the first hydrogen sensitive layer is above or below a first threshold. The first output section is optically coupled to the first hydrogen detection section for receiving light having interacted with the first hydrogen sensitive layer such that the received light depends on the optical response of the first hydrogen sensitive layer. The first output section being configured for outputting an output signal as a low-hydrogen output signal when the optical response corresponds to an amount of hydrogen below the first threshold, and as a high-hydrogen output signal, different from the low-hydrogen output signal, when the optical response corresponds to an amount of hydrogen above the first threshold. The optical response is at least one of a reflection and a transmission of the first hydrogen sensitive layer.

According to another aspect, an exemplary is disclosed wherein the sensor assembly can be used for sensing a status condition of electrical equipment. Herein, the sensor assembly is be, for example, immersed in the insulation liquid (e.g. in transformer oil of a transformer).

According to another aspect, an exemplary method of sensing a status condition of a liquid-filled electrical equipment such as a transformer is provided. The method can include the following: A first hydrogen detection section in communication with (e.g. immersed in) an insulation liquid of the electrical equipment is illuminated with light. A first hydrogen sensitive layer of the first hydrogen detection section interacts with the light, such that an optical response of the first hydrogen sensitive layer to the received light depends on whether an amount of hydrogen dissolved in the insulation liquid is above or below a first threshold. A first output section receives the light having interacted with the first hydrogen sensitive layer, whereby the received light depends on the optical response of the first hydrogen sensitive layer. If the optical response corresponds to an amount of hydrogen below the first threshold, the first output section outputs a low-hydrogen output signal. On the other hand, if the optical response corresponds to an amount of hydrogen above the first threshold, the first output section outputs a high-hydrogen output signal, different from the low-hydrogen output signal.

An sensor assembly and method as disclosed herein can allow for obtaining a good estimate of a condition of the electrical equipment and/or of its insulation liquid using a hardware setup that works reliably and involves only minimal calibration. Due to the optical detection, electrical interference can be avoided. Further, the system can include inexpensive optical components, and is therefore simple, cost-effective and robust, and does not have moving parts. The sensor assembly can be especially advantageous for the monitoring of oil-filled transformers.

In the following, some further general aspects of exemplary embodiments are described. Aspects and parts of aspects are independent of each other and can be combined in any manner. For example, any aspect or embodiment described in this document can be combined with any other aspect or embodiment.

First, some general possible aspects relating to the sensor assembly are described. The sensor assembly can be configured out adapted for sensing a status condition of an insulation-liquid-filled electrical equipment. Herein, electrical equipment refers to any equipment such as shunt reactors, bushings and transformers. Embodiments disclosed herein can, for example, be particularly suited for the insulation liquid being insulation oil. Disclosed embodiments are further, particularly suited for the electrical equipment being a transformer such as a power or distribution transformer, such as for an oil-filled transformer.

The status condition of the electrical equipment can be expressed by the hydrogen content of the insulation liquid, which is a reliable indicator of various conditions, such as fault conditions. The hydrogen content is defined as the amount of hydrogen dissolved in the insulation liquid (in ppm). The hydrogen sensitive layer is arranged in communication with the insulation liquid, for example, immersed in the insulation liquid, so that the amount of hydrogen dissolved in the insulation liquid results in a characteristic partial pressure of hydrogen at the hydrogen sensitive layer (e.g., the partial pressure in the insulation liquid at a position probed by the hydrogen sensitive layer), this partial pressure being a function of the hydrogen content (in ppm) in the insulation liquid. This relation may depend on additional parameters such as the temperature of the insulation liquid and/or of the hydrogen sensitive layer. Herein, the term "hydrogen" may refer to hydrogen molecules or atoms (which may be radicals).

Next, some aspects relating to the light source are described in more detail. Herein, light is defined as electromagnetic radiation. The radiation may have any wavelength, but is, for example, in the mid-IR, near-IR or visible wavelength range.

Next, some aspects relating to the hydrogen detection section are described in more detail. The hydrogen detection section, also referred to as the first hydrogen detection section herein, is optically coupled to the light source for receiving light from the light source. The hydrogen detection section has a (first) hydrogen sensitive layer that changes an optical response with respect to the received light depending on whether an amount of hydrogen at the hydrogen sensitive layer is above or below a predetermined (first) threshold. As stated above, the amount of hydrogen can be defined in terms of a partial pressure of hydrogen at the hydrogen sensitive layer which is directly related to an amount of hydrogen (in ppm) dissolved in the insulation liquid, and thereby expresses the status condition of the electrical equipment. For example, the (first) threshold may correspond to a threshold H content in the insulation liquid having a value between, for example, 50 ppm and 200 ppm. Alternatively, the value of the threshold H content in the insulation liquid may be between, for example, 350 ppm and 1200 ppm, or, for example, between 900 ppm and 3000 ppm. The threshold may depend on the temperature of the insulation liquid which influences the solubility of hydrogen therein. Herein, any condition on the threshold is defined at a reference temperature such as room temperature or standard operating temperature or some predetermined temperature, such as 40° C. According to a particular aspect, the threshold is in at least one of the ranges defined herein at any temperature between, for example, 20° C. and 80° C.

The sensor assembly can be configured such that the first hydrogen detection section is immersed, during operation, in the insulation liquid of the electrical equipment.

The optical response may include transmission, reflection, absorption and/or other properties detectable by the output section. A wavelength of light radiated from the light source remains unchanged after having interacted with the first hydrogen sensitive layer.

According to an aspect, the optical response is a reflection, and the hydrogen detection section (more precisely, its hydrogen sensitive layer) is mounted (laminated) on an end portion of a light guiding substrate coupling the hydrogen detection section to the light source and to the output section (possibly via other optical conducting materials as well).

According to another aspect, the optical response is a transmission, and the hydrogen detection section is mounted between a light guiding material coupling the first hydrogen detection section to the light source and a light guiding material coupling the first hydrogen detection section to the output section. In this manner, the hydrogen detection section is located in a light path between the light source and the output section.

According to an aspect, the hydrogen detection section includes, further to the hydrogen sensitive layer, at least one of an adhesion layer interposed between the first hydrogen sensitive layer and a light guiding substrate; a catalytic layer adjacent to the first hydrogen sensitive layer, the catalytic layer comprising a catalyst for splitting up hydrogen molecules to single H atoms (e.g. a layer comprising Pd, e.g. Pd—Au, Pd—Cu, Pd—Ag alloy or Pd); or a protection layer.

The protection layer may include an organic layer, such as a layer including PTFE, or an inorganic layer, such as a coating including $SiO_2$ and/or $Al_2O_3$. The protection layer may cover the first hydrogen sensitive layer (with potentially other layer(s), such as the catalytic layer, inbetween) on the hydrogen sensitive layer's insulation-liquid-facing side, for example, covering the entire insulation-liquid-facing side. The protection layer may be permeable for hydrogen, but less permeable (or not permeable) with respect to at least some other components of the insulation liquid, e.g. other gases dissolved therein such as $O_2$, $H_2S$ and/or CO.

The first hydrogen sensitive layer may include a metal or metal alloy that changes the optical response depending on whether the amount of hydrogen is above or below the first threshold. Such metals are Mg, Pd, Ti, La, Y, Gd or alloys thereof; e.g., Mg binary alloys such as MgM with M being a transition metal or Al and Mg ternary alloys such as MgNiTi; Pd alloys, such as PdAg, PdAu, PdCu; or pure elements such as Y, Gd, Pd, La. Further examples are Mg compounds such as Mg—Ni compounds and Mg—Ti compounds, or Mg, V, Y or (other) compounds thereof. Particular Mg—Ni compounds having this effect are $Mg_2Ni$. For example, $Mg_2Ni$ has a relatively high reflectivity, but under the influence of surrounding hydrogen at least a portion thereof is converted to $Mg_2NiH_4$, which is much less reflective at room temperature.

According to an aspect, the sensor assembly may include a plurality of hydrogen detection sections. Each of the hydrogen detection sections may be configured as described for the (first) hydrogen detection section.

Thus, the sensor assembly may include, in addition to the first hydrogen detection section, a second hydrogen detection section having a second hydrogen sensitive layer that changes an optical response to the received light depending on whether an amount of hydrogen dissolved in the insulation liquid is above or below a second threshold. Optionally, the sensor assembly may include a third hydrogen detection section having a third hydrogen sensitive layer that changes an optical response to the received light depending on whether an amount of hydrogen dissolved in the insulation liquid is above or below a third threshold. Each of the sensor assemblies may be optically connected to a common light source, and/or to a separate output section.

According to an exemplary embodiment, the thresholds (first, second and optionally third threshold and possibly further threshold(s)) are different from each other. For example, the first threshold may correspond to a threshold H content between, for example, 50 ppm and 200 ppm in the insulation liquid; the second threshold may correspond to a threshold H content between, for example, 350 ppm and 1200 ppm; and/or the third threshold may correspond to a threshold H content between, for example, 900 ppm and 3000 ppm. Alternatively or additionally, at least some of the thresholds may be the same, thereby increasing redundancy and thus reliability of the sensor system.

In the following, the (first) output section and related aspects are described in more detail. The output section is optically coupled to the hydrogen detection section for receiving light having interacted with the hydrogen sensitive layer, such that the light received by the output section depends on the optical response of the first hydrogen sensitive layer. The output section is configured for outputting an output signal as a low-hydrogen output signal when the optical response corresponds to an amount of hydrogen below the first threshold, and as a high-hydrogen output signal, different from the low-hydrogen output signal, when the optical response corresponds to an amount of hydrogen above the first threshold.

For example, the output section may output an essentially binary (or essentially discontinuous) output signal, triggered by the amount of light received therein which depends on the amount of hydrogen being below or above the (first) threshold. Herein, a binary signal is understood to be a signal that has a sharp transition at the threshold and that allows for determining the high- or low-hydrogen output signal but essentially no continuous signal information inbetween. Hence, the binary signal is essentially a "yes/no" type signal with a sharp transition between the "yes" and the "no" state. Herein, "sharp transition" may, for example, be defined as follows: The gradient of the output signal intensity as a function of hydrogen amount has a peak at the threshold, and the peak's half-width is less than 15% of the threshold value. For example, the output signal can be a discontinuous binary signal, e.g., jumping discontinuously at the threshold between the low-hydrogen output signal and the high-hydrogen output signal.

According to an aspect, the first output section includes a light detector for detecting the received light, and a signal analyser for analysing a detection signal of the light detector, wherein the signal analyser is configured for selectively outputting the low-hydrogen output signal or the high-hydrogen output signal in dependence of the detection signal (e.g. a detected intensity) of the light detector.

According to another aspect, the first output section includes a visual output element configured for displaying at least a portion of the light received from the first hydrogen sensitive layer as the output signal. Hence, the output signal has a sharp transition between the low-hydrogen output signal and the high-hydrogen output signal (essentially binary as defined above), because of the sharp transition of the optical response of the hydrogen sensitive layer at the first threshold. The transition can especially sharp in case of a phase transition between a low-hydrogen state and a high-hydrogen state.

In the following, the heater, thermostat unit and related aspects are described in more detail. Namely, according to an aspect, the sensor assembly can include a thermostat unit arranged for keeping a temperature of the first (and, if present, second, third, etc.) hydrogen detection section within a predetermined temperature range. The heater may be configured for being activated and/or deactivated periodically according to a temperature cycle.

According to a further aspect, the sensor assembly can include a temperature sensor for sensing the temperature of the insulation liquid, and/or a hydrogen detection section temperature sensor for sensing the temperature at the hydrogen detection section (hydrogen sensitive layer).

According to a further aspect, an electrical equipment with an insulation liquid is provided, wherein the sensor assembly described herein is immersed in the insulation liquid (e.g., partially immersed so that the hydrogen detection section is at least in partial contact with the insulation liquid).

Reference will now be made in detail to various embodiments, one or more examples of which are illustrated in each figure. Each example is provided by way of explanation and is not meant as a limitation. For example, features illustrated or described as part of one embodiment can be used on or in conjunction with any other embodiment to yield yet a further embodiment. It is intended that the present disclosure includes such modifications and variations.

Within the following description of the drawings, the same reference numbers refer to the same or to similar components. Generally, only the differences with respect to the individual embodiments are described. Unless specified otherwise, the description of a part or aspect in one embodiment applies to a corresponding part or aspect in another embodiment as well.

FIG. 1 is a schematic view of a transformer 1 with a sensor assembly 10 according to an exemplary embodiment disclosed herein. In FIG. 1 and the following Figures, a transformer is used as an example for the electrical equipment, but other insulation-liquid-filled electrical equipment, such as shunt reactors, bushings or the like may be used as well.

The transformer 1 has a housing defining an inner volume 4 which is filled with an insulation liquid such as insulation oil 2. In the following, insulation oil is used as an example of the insulation liquid, but the invention is not limited to insulation oil.

Within the housing, there is also an electrical component 6, e.g. the transformer core and windings. The insulation oil 2 may fill the entire housing or may extend within the housing up to a liquid line 5. In the latter case, an upper part above the liquid line 5 may be gas-filled. The housing may be sealed or connected to the ambient atmosphere, possibly through an overpressure valve.

As mentioned in the introductory section, it can be advantageous to have an on-line measurement of gases dissolved in the insulation oil 2. To this purpose, a sensor assembly 10 is provided. The sensor assembly 10 is (partially) immersed in the insulation oil 2, more precisely a hydrogen detection section 30 of the sensor assembly is immersed in the insulation oil 2.

Besides the hydrogen detection section 30, the sensor assembly 10 has a light source 40 and a first output section 50. The light source 40 and the first output section 50 are optically coupled to the first hydrogen detection section 30 via respective light guides 24 and 25 (optical fibers) and a substrate 20 on which the hydrogen detection section 30 is mounted.

The substrate 20 is at least partially transparent to light from the light source 40. Hence, the light source 40 illuminates the hydrogen detection section 30 via the light guide 24 and the substrate 20, and the output section 50 receives radiation reflected from the hydrogen detection section 30 via the substrate 20 and the light guide 25.

The substrate 20 may be formed from a light guide (optical fiber(s)). The substrate 20 may be an end portion of (extend to) the light guides 24, 25 coupling the first hydrogen detection section 30 to the light source 40 and to the output section 50. Alternatively, the substrate 20 may be formed from a separate element to which the light guides 24, 25 (e.g. fibers) are joined. For example, the substrate 20 may include glass or a transparent crystal (e.g., of Si and/or $CaF_2$).

Figure 2:
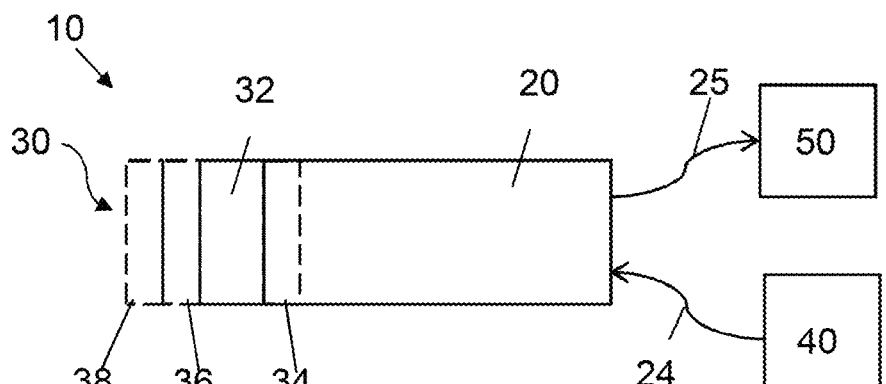
FIG. 2 is a schematic view of a sensor assembly according to an exemplary embodiment disclosed herein.

FIG. 2 shows the exemplary hydrogen detection section 30 in more detail. Here, it can be seen that the hydrogen detection section 30 includes a hydrogen sensitive layer 32 coated on an end portion of the substrate 20. The hydrogen sensitive layer 32 changes its reflectivity depending on an amount of hydrogen: If the amount of hydrogen at the first hydrogen sensitive layer 32 is below a first threshold, the hydrogen sensitive layer 32 is strongly reflective, and if the amount of hydrogen is above the first threshold, the hydrogen sensitive layer 32 is visibly less reflective. Thereby, the light from the light source 40 is either reflected (reflection mode) at the hydrogen sensitive layer 32 or goes through (transmission mode) the hydrogen sensitive layer 32. More generally, the reflection mode is characterized by a larger fraction of the light being reflected, and the transmission mode is characterized by a visibly smaller fraction of the light being reflected. Herein, the term reflection is to be understood broadly as light propagating back to the substrate 20 and ultimately to the output section 50, irrespective of the detailed mechanism causing the light to propagate back.

The hydrogen sensitive layer 32 may switch its optical response between these modes abruptly, depending on whether the amount of hydrogen at the hydrogen sensitive layer 32 is below or above the first threshold.

A suitable material of the hydrogen sensitive layer 32 is a metal or metal alloy that changes the optical response depending on whether the amount of hydrogen is above or below a first threshold. Such metals include, for example, Mg, Pd, Ti, a rare earth element such as La, Y, Gd, or alloys thereof. Particular examples of such alloys are Mg binary alloys such as MgM with M being a transition metal or Al; Mg ternary alloys such as MgNiTi; and Pd alloys such as PdAg, PdAu, or PdCu.

Figure 3:
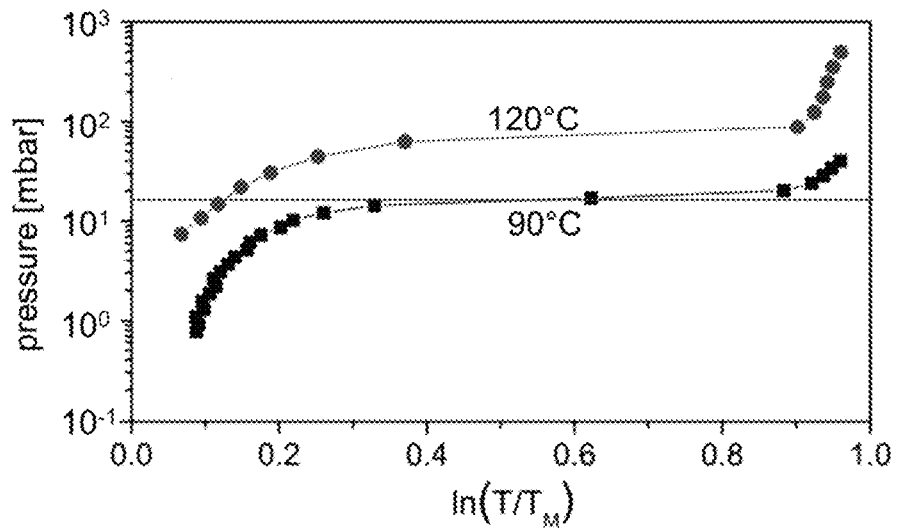
FIG. 3 is a diagram showing an exemplary optical response as a function of hydrogen partial pressure.

FIG. 3 illustrates the optical response of a hydrogen sensitive layer being a thin Mg alloy layer with a catalytic Pd layer thereon, as a function of hydrogen partial pressure at the hydrogen sensitive layer. Here, the optical response is shown as the optical transmission T relative to a reference transmission $T_M$, $T_M$ being the optical transmission in the hydrogen-free initial state. With this material, the reflection is inversely related to the transmission (i.e., low transmission corresponds to high reflection and vice versa). The transmission T is shown for two exemplary temperatures, 90° C. (squares) and 120° C. (circles).

Further, a horizontal line shows a threshold at about 18 mbar partial pressure of hydrogen for the temperature 90° C., at which the optical response jumps abruptly from reflective (low values of T) to transmissive (high values of T). This threshold corresponds to about 900 ppm hydrogen in mineral oil, assuming a bulk oil temperature of 40° C. and an Ostwald coefficient of 0.05.

Hence, the output section outputs an essentially binary (or essentially discontinuous) "yes/no" type output signal, depending on the transmission (or reflection) coefficient, and thereby on whether the amount of hydrogen is below or above the threshold, with a sharp transition therebetween. This can pose a significant advantage over continuous detectors: Since the hydrogen detection section needs to be calibrated only to a single threshold, calibration is easy to perform and stable. Also, the threshold is at a hydrogen amount of maximum sensitivity of the sensor, hence the signal to noise ratio is excellent.

Thus, in stark contrast to a continuous signal that would allow obtaining an (approximate) numerical value of the hydrogen content, the information content of the output signal is lower (binary yes/no signal) but more reliable. If additional information about the hydrogen content is desired based on the binary information provided by the output section, a plurality of hydrogen detection sections (and output sections) of different thresholds can be provided, as is described in more detail with reference to FIG. 7 below.

Referring back to FIGS. 1 and 2, the hydrogen detection section 30 is optically coupled to the output section 50 via the light guide (fiber(s)) 20, 25. The portion 20 of the light guide is also referred to as substrate, and may be integral with the portion 24, 25 or provided as a separate piece coupled thereto. The output section 50 is configured for outputting a low-hydrogen output signal or a high-hydrogen output signal in dependence of the optical response of the hydrogen detection section 30 (hydrogen sensitive layer 32): Namely, when the output section 50 receives a large amount of reflected light from the hydrogen sensitive layer 32 (i.e. the hydrogen content is below the threshold, such that the hydrogen sensitive layer 32 is in reflection mode), the output section 50 outputs a low-hydrogen output signal. In contrast, when the output section 50 receives a small amount of reflected light from the hydrogen sensitive layer 32 (i.e. the hydrogen content above threshold such that the hydrogen sensitive layer 32 is in transmission mode), the output section 50 outputs a high-hydrogen output signal.

Next, possible implementations of the output section 50 are described in connection to FIGS. 4a and 4b. FIG. 4a shows an output section 50 according an exemplary embodiment which includes a light detector 52 and a signal analyser 54 operatively connected to a display 56. The light detector 52 is connected to the hydrogen sensitive layer 32 via the light guide 20, 25 (see FIG. 2) for detecting the reflected light from the hydrogen sensitive layer 32. The light detector 52 outputs a detection signal indicative of the detected amount of light to the signal analyser 54.

The signal analyser 54 then analyses the detection signal and determines whether the amount of light is (a) above a light threshold (indicating reflection mode of hydrogen sensitive layer 32, i.e. a hydrogen content below threshold) or (b) below a light threshold (indicating transmission mode of hydrogen sensitive layer 32, i.e. a hydrogen content above threshold). In case (a), the signal analyser 54 outputs a low-hydrogen output signal, and in case (b), the signal analyser 54 outputs a high-hydrogen output signal. This output signal is then output to the display 56.

FIG. 4b shows an alternative and simpler output section 50 that includes a visual output element 150 which displays the light received from the first hydrogen sensitive layer 32 directly. Hence, (a) if the hydrogen sensitive layer 32 is in reflection mode (i.e. a hydrogen content below threshold), a large amount of light is reflected by the hydrogen sensitive layer 32 and reaches the visual output element 150. Correspondingly, a bright visual signal is displayed by the visual output element 150. In contrast, (b) if the hydrogen sensitive layer 32 is in transmission mode (i.e. a hydrogen content above threshold), a small amount of light is reflected by the hydrogen sensitive layer 32 and reaches the visual output element 150. Correspondingly, the visual output element 150 remains dark.

The output section 50 of FIG. 4b can have an advantage that it can be used without any readout electronics by simply detecting visually the light reflected or transmitted from the hydrogen sensitive layer 32. Since the latter changes its properties upon exceeding a certain gas level, the optical properties of the hydrogen sensitive layer 32 can be tuned such that the hydrogen sensitive layer 32 changes, e.g., from reflecting to transparent.

In the following, some further details and possible exemplary variants of the sensor assembly will be described. First, again with reference to FIG. 2, some variants of the hydrogen detection section 30 with additional layers are discussed. According to a variant, the sensor can have an optional catalytic layer 36 adjacent to (on top of) the hydrogen sensitive layer 32 that allows facilitating the hydrogen dissociation of hydrogen molecules in hydrogen atoms that diffuse into the hydrogen sensitive layer. Thus, the catalytic layer 36 can include a catalyst material for splitting up hydrogen molecules ($H_2$) to single H atoms. Such catalyst material may include, for example, Pd, Pt, Ni, or a combination thereof. An exemplary catalyst material is a Pd compound such as a Pd—Au, Pd—Cu or Pd—Ag alloy, the alloy optionally including still further elements.

In an alternative variant, the functionality of the catalytic layer 36 can also be integrated in the hydrogen sensitive layer 32, (e.g., the catalytic functionality and the optical-response-changing functionality may be provided in a single hydrogen sensitive layer 32). For example, a layer 32 including Pd (e.g. a Pd-transition metal alloy, such as a Pd—Au, Pd—Ag, and/or Pd—Cu) has these double functionalities.

Additionally or alternatively, the sensor can have an optional protective coating 38 on top of the catalytic layer 36 or on top of the hydrogen sensitive layer 32, to protect it from corrosion or decrease the contamination from other gases like $O_2$, $H_2S$ or CO. This protective coating can be gas permeable allowing the gases to reach the hydrogen sensitive layer while limiting other components of the insulation liquid from doing so. The protective coating 38 may have the additional effect of balancing the hydrogen and oxygen content at the catalytic surface. In a specific example, the protective coating 38 may be provided as an organic coating, such as a coating layer comprising PTFE, or an inorganic coating, such as a coating layer including $SiO_2$ and/or $Al_2O_3$. For example, the protective coating completely covers the hydrogen sensitive layer 32, optionally with other layer(s), such as the catalytic layer 36, between the hydrogen sensitive layer 32 and the coating 38.

Additionally or alternatively, an adhesion layer 34 such as a thin Ti layer may optionally be provided between the hydrogen sensitive layer 32 and the substrate 20.

In a further embodiment, the hydrogen detection section 30 (layer 32) may also be provided in a gas-filled portion that communicates with the insulation liquid so that the amount of hydrogen in the gas-filled portion is indicative of the amount of hydrogen in the insulation liquid. For example, the hydrogen detection section 30 (layer 32) may be provided in the head space above line 5 in FIG. 1. Since the amount of hydrogen present in the head space depends directly on the amount of hydrogen dissolved in the insulation oil 2, the hydrogen measurement in the headspace is also capable of indicating the amount of hydrogen dissolved in the insulation oil 2 relative to a predetermined threshold. For example, the hydrogen detection section 30 may be provided at any position that is in such communication with the insulation oil 2 that the amount of hydrogen at the hydrogen detection section 30 is a direct function of the amount of hydrogen dissolved in the insulation oil 2. However, in order to obtain a reliable measurement that depends on as few external factors as possible, it can be preferred that the hydrogen detection section 30 is operable when immersed into the insulation oil, without any gas chamber between the insulation oil and the hydrogen sensitive layer 32.

While the above description was directed to a reflection measurement, the measurement may be modified to include a measurement of other optical properties of the hydrogen sensitive layer. Hence, the above description may be generalized by measuring any optical property of the hydrogen sensitive layer in place of the reflectivity mentioned herein. For example, if the hydrogen detection section 30 is adapted to reflect at least some of the light having passed the hydrogen sensitive layer 32, the measurement may be also sensitive to a change in other optical properties of the hydrogen sensitive layer 32, such as transmission and absorption. Another example of measuring another optical property, a transmission measurement, is described in the following.

The hydrogen detection section 30 (30a, 30b, 30c) is illuminated by light from the light source 40. Therefore the different layers like the adhesion layer 34, the catalytic layer 36, the protective coating 38 and, for example, the hydrogen sensitive layer 32 are arranged in the light path of light source 40 and the light guide 24 as visible in FIGS. 2 and 3. The different layers 32, 34, 36 and 38 of the hydrogen detection section 30 are arranged substantially in a plane perpendicular to the propagation direction of the light, in the possible reflection mode or the transmission mode.

Figure 5:
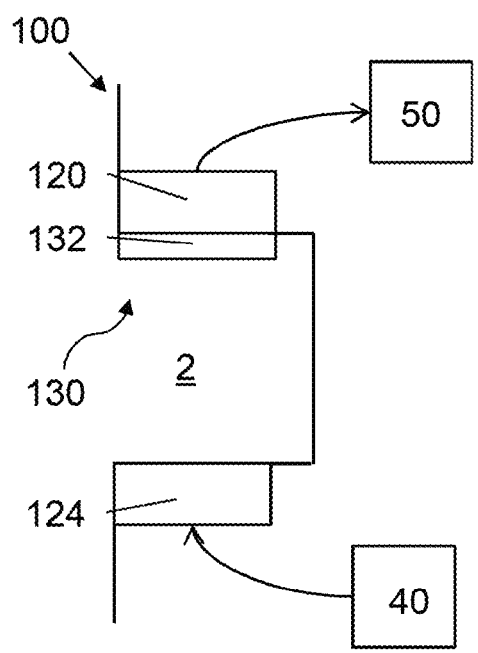
FIG. 5 is a schematic view of a sensor assembly according to an exemplary embodiment disclosed herein configured and adapted for a transmission measurement.

FIG. 5 illustrates a further variant of the sensor assembly 100 adapted for a transmission measurement, in contrast to the reflection measurement shown in FIG. 2. Only the differences with respect to FIG. 2 shall be described. Namely, in the hydrogen-detection section 130 of FIG. 5, a chamber for the insulation oil 2 is formed, and two substrates—emitter substrate 124 and receiver substrate 120—are arranged to face each other through the chamber. The substrates 120, 124 may comprise glass, Si and/or $CaF_2$.

Further, a hydrogen sensitive layer 132 is provided on a side of the receiving substrate 120 such as to be in contact with the insulation liquid 2. The hydrogen sensitive layer 132 corresponds to the layer 32 shown in FIG. 2. Hence, an optical response (here: light transmittivity) of the hydrogen sensitive layer 132 changes depending on whether the amount of hydrogen at the first hydrogen sensitive layer 132 is above or below the first threshold. The hydrogen sensitive layer 132 may be partially or fully immersed in the insulation oil 2, i.e. contact the insulation oil 2.

The detection section 130 may be configured in any manner as described herein, e.g. with reference to FIG. 2. Hence, the detection section 130 may, for example, optionally include further layers such as a protection layer, catalytic layer, adhesion layer etc. as shown in FIG. 2.

The emitter substrate 124 is optically connected to the light source 40 via a light conductor (optical fiber), and the receiver substrate 120 is optically connected to the output section 50 via another light conductor (optical fiber), such that the radiation detection section 50 detects radiation from the radiation source 40 which has been transmitted through the insulation oil 2 and the hydrogen sensitive layer 132.

Hence, a low optical transmittivity received at the output section 50 may indicate an amount of hydrogen below the first threshold, and a high optical transmittivity may indicate an amount of hydrogen above the first threshold, as shown in FIG. 3. The output section 50 may then output, depending on the amount of light received, either a low-hydrogen output signal (if low amount of light received indicating low transmittivity) or a high-hydrogen output signal (if high amount of light received indicating high transmittivity). This may be achieved by the output signals of the output sections described above in conjunction with FIGS. 4a and 4b, wherein "high-hydrogen output signal" is replaced by "low-hydrogen output signal" and vice versa.

Other variations of the detection section 130 of FIG. 5 are possible. For example, the hydrogen sensitive layer 132 may be mounted on the light guiding material 124 instead of the material 120, or in some other place between the materials 120 and 124. As a general principle independent of the specific implementation of the transmission configuration, the hydrogen sensitive layer 132 can, for example, be arranged in a light path from the light source 40 to the output section 50.

Figure 6:
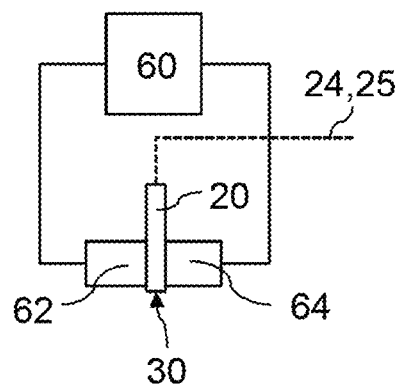
FIG. 6 is a schematic view of a sensor assembly according to an exemplary embodiment disclosed herein including a thermostat assembly.

FIG. 6 is a schematic view of a sensor assembly according to an exemplary embodiment disclosed herein as including a thermostat unit. The thermostat unit includes a heater 62, a temperature sensor 64 and a control unit 60. The heater 62 is arranged for heating the hydrogen detection section 30. To this purpose, the heater 62 is, for example, provided in direct solid contact with the hydrogen detection section 30.

The temperature sensor 64 is provided for detecting a temperature at the hydrogen detection section 30, for example, at the hydrogen sensitive layer 32. The arrangement of the heater 62 and temperature sensor 64 in FIG. 6 are schematic, and the elements can be arranged in any other manner as long as they are in close thermal contact with the hydrogen detection section 30. For example, the heater 62 is, for example, isolated from the insulation oil 2 and/or from the hydrogen detection section 30.

The heater controller 60 is connected to the heater 62 for controlling operation of the heater 62, and connected to thermometer 64 for receiving the measured temperature. In a thermostat mode, the heater controller 60 controls the heater 62 in dependence of a signal from the thermometer 64 such that the hydrogen detection section 30 (thermometer 64) is kept at a predetermined temperature or within a predetermined temperature range. Hence, the control unit 60 is configured for activating the heater 62 when the temperature measured by the temperature sensor 64 falls below a predetermined lower temperature threshold, and for de-activating the heater when the temperature is above a predetermined upper temperature threshold.

A further thermometer (e.g., oil temperature sensor) may be provided for measuring the temperature of the surrounding insulation fluid 2. Alternatively or additionally, the control unit 60 may be configured for switching the heater 62 off periodically, so that the temperature sensor 64 may reach thermal equilibrium with the surrounding insulation fluid 2 for measuring its temperature.

The heater controller 60 may also operate in other modes. For example, the heater controller 60 may be operated to vary the temperature in response to a signal from the signal analyser 54 (see FIG. 4*a*). According to an example, the temperature may be controlled (within a predetermined temperature interval) according to a feed-back signal from the signal analyser 54 so that the optical response of the hydrogen sensitive layer 32 is always kept at/near the threshold. Hence, the heater can be controlled to keep the hydrogen sensitive layer 32 at the threshold temperature at which the optical response of the hydrogen sensitive layer 32 is changed for the current $H_2$ concentration. From this temperature, and from the temperature of the surrounding insulation fluid 2, the signal analyser 54 is capable of calculating a numerical value for the hydrogen content using pre-stored solubility factors of hydrogen at the respective temperature. This mode has an advantage of avoiding a large number of phase transitions (or crossovers) of the hydrogen sensitive layer 32, if the hydrogen concentration would otherwise fluctuate about the threshold concentration at a given constant temperature.

According to another mode, referred to as a sweeping mode, the temperature of the hydrogen detection section 30 is gradually increased from a first (low) temperature to a second (high) temperature. Thereby, the optical response of the hydrogen sensitive layer 32 will change from non-reflective to reflective at a threshold temperature depending on the $H_2$ concentration (if the $H_2$ concentration is in a detectable range) and thus indicative of the $H_2$ concentration. Correspondingly, according to this embodiment, the signal analyser 54 (see FIG. 4*a*) is capable of determining the threshold temperature at which the optical response of the hydrogen sensitive layer 32 is changed. Then, the signal analyser 54 is capable of calculating, from the threshold temperature and from the temperature of the surrounding insulation fluid 2, a numerical value for the hydrogen content using pre-stored solubility factors of hydrogen and at the respective temperature.

According to another mode, referred to as a cleaning mode, the heater controller 60 is configured (i.e., adapted) for controlling the heater 62 to heat the layer 32 to a high temperature at which all or a substantial portion of hydrogen and/or moisture and/or contaminants desorb(s) from the layer 32, for a limited amount of time. The controller may be adapted to initiate the cleaning mode periodically or when a cleaning condition is met.

According to another mode, referred to as a health-check mode, the health status of the hydrogen sensitive layer 32 can be checked using the heater 62. Namely, the layer 32 can age due to thermal influences, chemical influences (e.g. acid substances in the oil) or due to an abundant amount of moisture or oxygen. In order to perform a health check of the hydrogen sensitive layer 32, first the cleaning mode is performed. Then, the signal analyser 54 (see FIG. 4*a*) is adapted to compare a measured optical property (e.g. reflectivity/transmission) with a stored reference optical property corresponding to a healthy layer.

In the case of several hydrogen detection sections (such as in the embodiment of FIG. 7), the heater 62 may either be placed in the vicinity of, for example, in solid contact with, the several hydrogen detection sections, or several heaters may be provided (either individually or jointly activated and deactivated), one for each hydrogen detection section.

The heater 62 allows the sensor to be kept at an approximately constant temperature. In this manner, a change in the hydrogen threshold (e.g., the hydrogen concentration at which the material switches the optical properties) due to temperature fluctuations can be avoided or at least reduced.

On the other hand, depending on the accuracy level of the sensor it is also possible not to control the temperature of the hydrogen detection section if the variation of the threshold concentration with temperature is acceptable. As an example, the hydrogen threshold concentration for Mg to $MgH_2$ would change only from 20 ppm to 30 ppm between 40° C. and 80° C. More generally, a tolerance in a similar range (e.g., increase by about 50 between 40° C. and 80° C.) is expected without temperature compensation. Depending on the desired accuracy, such a tolerance could be acceptable.

FIG. 7 is a schematic view of a sensor assembly according to an exemplary embodiment having multiple (here: three) hydrogen detection sections 30*a*, 30*b*, 30*c*. Each of these hydrogen detection sections 30*a*, 30*b*, 30*c* has a respective hydrogen sensitive layer 32*a*, 32*b*, 32*c* mounted on a substrate 20*a*, 20*b*, 20*c*. The hydrogen detection sections 30*a*, 30*b*, 30*c* are optically coupled to a common light source 40 but may alternatively also be coupled to respective individual light sources. Further, the hydrogen detection sections 30*a*, 30*b*, 30*c* are optically coupled to respective output sections 50*a*, 50*b*, 50*c* via light guides (respective substrate 20*a*, 20*b*, 20*c* and respective light guide 50*a*, 50*b*, 50*c*). Thereby, the output section 50*a* receives light having interacted with the first hydrogen sensitive layer 32*a* and depending on the optical response of the first hydrogen sensitive layer 32*a*; and similarly the output sections 50*b*, 50*c* receive light having interacted with the hydrogen sensitive layer 32*b*, 32*c* and depending on the optical response of the hydrogen sensitive layer 32*b*, 32*c*, respectively.

In this manner, each of the output sections 50a, 50b, 50c outputs a low-hydrogen output signal when the amount of hydrogen at its respective hydrogen sensitive layer 32a, 32b, 32c is below its respective threshold, and outputs a high-hydrogen output signal in the opposite case.

In an exemplary embodiment, the thresholds of the respective hydrogen sensitive layers 32a, 32b, 32c are different from each other. In this manner, different fault conditions can be distinguished by identifying which thresholds for the hydrogen content are being exceeded, and which are not being exceeded. For example, if the first threshold (of hydrogen sensitive layer 32a) is at about 100 ppm hydrogen; the second threshold (of hydrogen sensitive layer 32b) is at about 800 ppm hydrogen; and the third threshold (of hydrogen sensitive layer 32c) is at about 1800 ppm hydrogen, the conditions 1-4 mentioned in Table 1 can be distinguished:

Below 100 ppm hydrogen, (i.e., the condition 1 of Table 1) all hydrogen sensitive layers 32a, 32b, 32c are reflecting and the light is reflected to all of the output sections 50a, 50b, 50c which therefore output a low-hydrogen output signal. At concentrations above 100 ppm, but still below 700 ppm (condition 2) only the hydrogen sensitive layer 32a will switch from reflective to absorbing (or transparent), so that the output section 50a now outputs a high-hydrogen output signal. In contrast, the output sections 50b, 50c still output a low-hydrogen signal because the respective hydrogen sensitive layers 32b, 32c are still reflecting. In this way, the sensor can detect each of the risk conditions of Table 1 depending on the number of sensors that output the low- or high-hydrogen output signal.

More generally, according to an exemplary aspect disclosed herein, a first threshold, for example, corresponds to an H content of 50 ppm to 200 ppm in the insulation liquid. Further, in the case of more than one hydrogen sensitive layer, a second threshold, for example, corresponds to an H content of 350 ppm to 1200 ppm in the insulation liquid. Further, a third threshold, for example, corresponds to an H content of 900 ppm to 3000 ppm in the insulation liquid. These thresholds are defined at a reference temperature such as room temperature or standard operating temperature or some reference temperature such as 40° C.

The thresholds can be adapted to a desired threshold value as follows: For example, alloying the metal (e.g. Mg or Pd) with various transition metals allows to tune the threshold of hydrogen detection from 20 ppm of hydrogen in oil (pure magnesium hydrogen sensitive layer) to 1800 ppm (magnesium-nickel-titanium alloy), with intermediate thresholds at 100 ppm (magnesium-vanadium alloy) or 800 ppm (magnesium-titanium alloy, see FIG. 3). By varying the element concentrations between these alloys, intermediate threshold values for the hydrogen concentration can be obtained.

Apart from the selection of a sensing material, mechanical effects induced by clamping of the hydrogen sensitive layer to its support can be used to tune the detection level of the sensor: hydrogen sensitive layer thickness, degree of adhesion to the substrate and to the top catalytic layer, morphology and microstructure (e.g. layer growth mode, grain size, crystallographic orientation, porosity) have all an influence on the hydrogen threshold detection level. This means the same material can be used for obtaining different thresholds.

The hydrogen detection sections 30a, 30b, 30c and the output sections 50a, 50b, 50c of FIG. 7 can be realized in any manner described herein, e.g. in the manner described in relation to any of FIGS. 2-6. Also, any other number of hydrogen detection sections 30a, 30b, 30c and output sections 50a, 50b, 50c can be provided, e.g. one hydrogen detection section or a plurality of hydrogen detection sections. For example, at least some of the plurality of hydrogen detection sections have mutually different thresholds, such as different by at least a factor of 2 in terms of ppm hydrogen in the insulating liquid.

The embodiment of FIG. 7 can be varied in various manners. For example, the plurality of hydrogen detection sections 30a, 30b, 30c may be mounted on a single common substrate instead of individual substrates 20a, 20b, 20c.

Also, in addition some hydrogen sensitive layers may be provided that are sensitive to other gases, either alone or in combination with hydrogen or yet other gases. Such additional hydrogen sensitive layers allow for obtaining even more detailed information about the status condition (see Table 1) and/or allow for identifying misreadings due to cross-sensitivities of the (first or other) hydrogen sensitive layer with respect to other gases.

Exemplary advantages of various embodiments of a sensor assembly as disclosed herein are:

- It can be directly inserted in insulation liquid without needing a gas/insulation liquid separation membrane or without needing a separation chamber for headspace measurements. On the other hand the sensor can also be used even in gas phase.
- Being an optical sensor, it is immune to electro-magnetic interference.
- It is simple in manufacturing, because the hydrogen sensitive layer is tuned only to one specific hydrogen concentration where it switches and does not need to address a large dynamic concentration range.
- It can be used in a redundant way, increasing the reliability, by using a plurality of hydrogen detection sections having the same threshold (either on a common substrate or on different substrates).
- It does not need any external gas supply for the functioning of the sensor (compared to e.g. TCD or pellistors).
- It can be easily calibrated.
- Calibration on the field can be reduced since the threshold sensor is not expected to drift as much as a continuous sensor.
- Most of the faults and aging processes of insulation-liquid-filled electrical apparatuses produce hydrogen gas and can be related to substantially different hydrogen content as shown in Table 1 above.
- Another advantage is that it allows reliable online measurement of crucial health information of the electrical equipment. This online measurement also allows for monitoring multiple transformers at a monitoring site. Any warnings or alerts allow initiating, in a timely manner, maintenance or repairs to the equipment concerned. Thereby the reliability of the entire installation is improved, and the risk of potentially very costly faults is reduced.

While the foregoing is directed to embodiments, other and further embodiments may be devised without departing from the basic scope determined by the claims.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A sensor assembly for sensing a status condition of a liquid-filled electrical equipment, the sensor assembly comprising:
   a light source;
   a first hydrogen detection section, the first hydrogen detection section being optically coupled to the light source for receiving light from the light source, wherein the first hydrogen detection section has a first hydrogen sensitive layer where the received light passes through the first hydrogen sensitive layer in a transmission mode and the first hydrogen sensitive layer abruptly switches an optical response between transmission and reflection with respect to light received at the first hydrogen sensitive layer depending on whether an amount of hydrogen at the first hydrogen sensitive layer is above or below a first threshold; and
   a first output section optically coupled to the first hydrogen detection section for receiving light having interacted with the first hydrogen sensitive layer such that received light depends on the optical response of the first hydrogen sensitive layer, the first output section being configured for outputting an output signal as a low-hydrogen output signal when the optical response corresponds to an amount of hydrogen below the first threshold, and as a high-hydrogen output signal, different from the low-hydrogen output signal, when the optical response corresponds to an amount of hydrogen above the first threshold, wherein the optical response is at least one of a reflection and a transmission of the first hydrogen sensitive layer, and wherein the first hydrogen detection section is immersed in an insulation liquid.

2. The sensor assembly according to claim 1, wherein the first output section comprises:
   a light detector for detecting the received light; and
   a signal analyser for analysing a detection signal of the light detector, wherein the signal analyser is configured for selectively outputting the low-hydrogen output signal or the high-hydrogen output signal in dependence of the detection signal of the light detector.

3. The sensor assembly according to claim 1, wherein the first output section comprises:
   a visual output element configured for displaying at least a portion of light received from the first hydrogen sensitive layer as the output signal.

4. The sensor assembly according to claim 1, configured such that a wavelength of light radiated from the light source will remain unchanged after having interacted with the first hydrogen sensitive layer.

5. The sensor assembly according to claim 4, configured for the optical response as a reflection, wherein the first hydrogen detection section is mounted on an end portion of a light guiding substrate, the substrate coupling the first hydrogen detection section to the light source and to the output section.

6. The sensor assembly according to claim 4, configured for the optical response as a transmission, wherein the first hydrogen detection section is mounted between a light guiding material coupling the first hydrogen detection section to the light source and a light guiding material coupling the first hydrogen detection section to the output section.

7. The sensor assembly according to claim 1, wherein the first hydrogen detection section is configured for being immersed in an insulation liquid of the electrical equipment.

8. The sensor assembly according to claim 1, wherein the first hydrogen detection section comprises at least one of:
   an adhesion layer interposed between the first hydrogen sensitive layer and a light guiding substrate;
   a catalytic layer adjacent to the first hydrogen sensitive layer, the catalytic layer having a catalyst for splitting up hydrogen molecules to single H atoms; and
   a protection layer covering the first hydrogen sensitive layer and being selectively permeable for hydrogen but not for, or less for, at least some other component of the insulating liquid.

9. The sensor assembly according to claim 1, comprising:
   a second hydrogen detection section having a second hydrogen sensitive layer that changes an optical response to the received light depending on whether an amount of hydrogen dissolved in the insulation liquid is above or below a second threshold.

10. The sensor assembly according to claim 9, comprising:
    a third hydrogen detection section having a third hydrogen sensitive layer that changes an optical response to the received light depending on whether an amount of hydrogen dissolved in the insulation liquid is above or below a third threshold.

11. The sensor assembly according to claim 10, wherein the first and second, and third thresholds are different from each other.

12. The sensor assembly according to claim 1, wherein the first threshold corresponds to an H content of 50 ppm to 200 ppm in the insulation liquid.

13. The sensor assembly according to claim 1, wherein the hydrogen sensitive layer comprises:
    a metal or metal alloy that changes the optical response depending on whether the amount of hydrogen is above or below a first threshold, the metal or metal alloy being at least one of Mg, Pd, Ti, a rare earth element including La, Y, Gd, or an alloy thereof.

14. The sensor assembly according to claim 1, comprising:
    a thermostat unit arranged for keeping a temperature of the first hydrogen detection section within a predetermined temperature range.

15. The sensor assembly according to claim 1, in combination with:
    a transformer, the sensor assembly sensing a status condition of the transformer, and the sensor assembly being immersed in transformer oil of the transformer as the insulation liquid.

16. A method of sensing a status condition of a liquid-filled electrical equipment, the method comprising:
    illuminating a first hydrogen detection section being immersed in insulation liquid of the electrical equipment with light, whereby a first hydrogen sensitive layer of the first hydrogen detection section interacts with the light, such that an optical response of the first hydrogen sensitive layer switches abruptly between light passing through in a transmission mode and reflection in respect to light received at the first hydrogen sensitive layer depending on whether an amount of hydrogen dissolved in the insulation liquid is above or below a first threshold;
    supplying a first output section with the light that has interacted with the first hydrogen sensitive layer, whereby light received by the output section depends on the optical response of the first hydrogen sensitive layer; and
    if the optical response corresponds to an amount of hydrogen below the first threshold, outputting via the first output section a low-hydrogen output signal, and if the optical response corresponds to an amount of hydrogen above the first threshold, outputting via the first output section a high-hydrogen output signal, different from the low-hydrogen output signal, the optical response being at least one of a reflection and a transmission of the first hydrogen sensitive layer.

17. The sensor assembly according to claim 1, wherein the first hydrogen detection section comprises a catalytic layer adjacent to the hydrogen sensitive layer that allows facilitating the hydrogen dissociation of hydrogen molecules.

\* \* \* \* \*